Aug. 22, 1972 J. H. McINTYRE Plant Pat. 3,258
MAPLE TREE
Filed Nov. 5, 1970
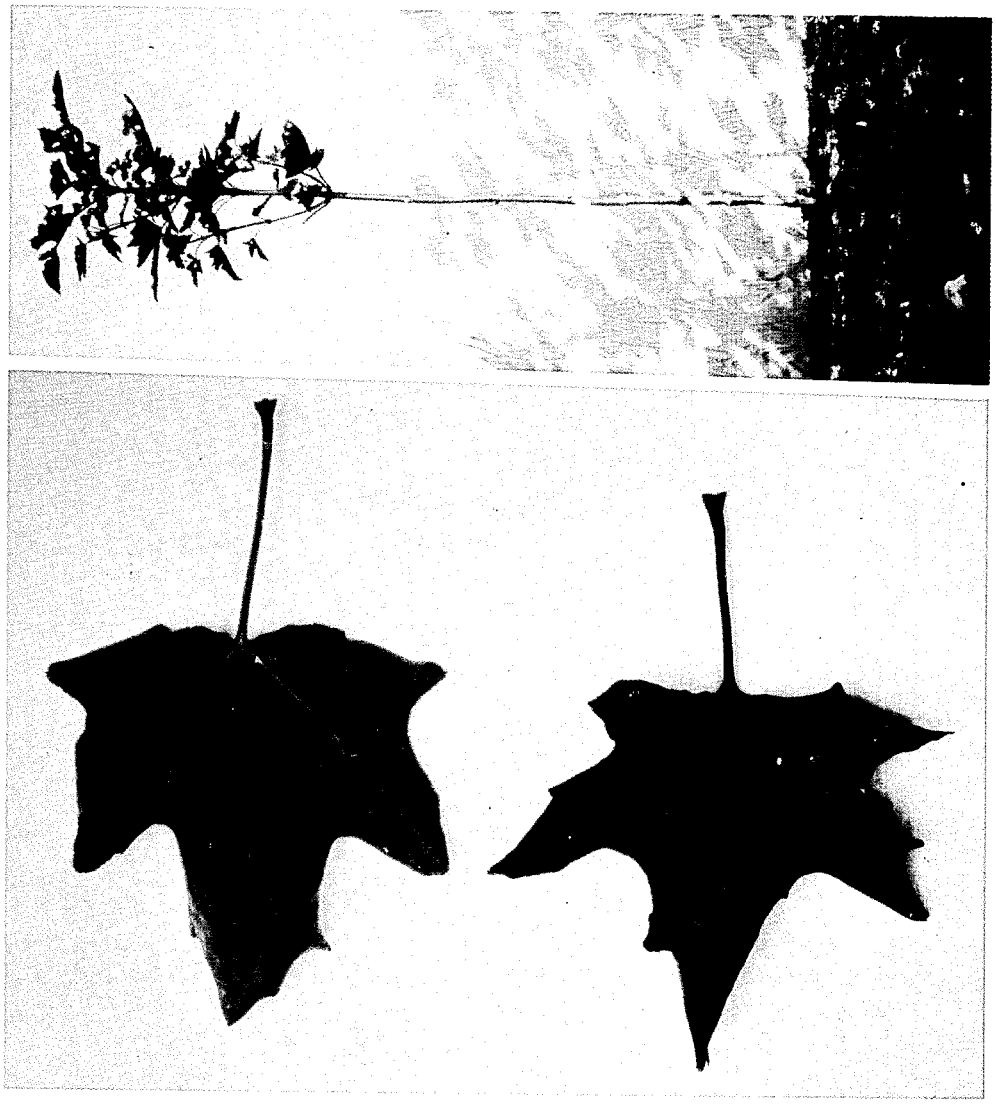
Inventor.
J. H. McIntyre
By: Robb & Robb
attorneys.

United States Patent Office

Plant Pat. 3,258
Patented Aug. 22, 1972

3,258

MAPLE TREE

John H. McIntyre, Gresham, Oreg., assignor to The W. E. McGill Trust, doing business as A. McGill and Son, Fairview, Oreg.

Filed Nov. 5, 1970, Ser. No. 87,363
Int. Cl. A01h *5/00*
U.S. Cl. Plt.—51 1 Claim

The present invention relates to a new and distinct variety of maple tree which was discovered by me as a cultivated bud mutation or sport of the maple variety known as "Crimson King" (Plant Patent No. 735), said discovery occurring in the nursery fields of my assignee located at Fairview, Oreg.

At the time of my discovery, a field of maple understocks had been budded to "Crimson King" under my direction and supervision, and in the course growing the same, my attention was attracted to one particular plant which exhibited an unusually profuse branching habit and a columnar form quite different from the other plants. On close observation of this particular plant, I found that it had apparently mutated or sported, so I carefully preserved the same and kept it under close observation. In due course, I asexually reproduced the sport by budding in the nursery aforementioned. Continued observations of the original sport and its progeny convinced me that it was a new variety which was definitely distinguished from its parent variety "Crimson King," as well as from all other maple varieties of which I am aware, as evidenced by the following combination of characteristics which are outstanding in the new variety:

(1) A more profuse branching habit than is normal for the species botanically known as Acer platanoides and commercially known as "Crimson King," with all branches being of an upright nature and making the tree a fastigiate or columnar type;
(2) Smaller leaves than those typical of "Crimson King," and said leaves being more cupped in form; and
(3) Although the leaves are 5-lobed, the lower 2 lobes are very small and make the leaves appear 3-lobed in effect.

The accompanying drawing shows a typical young tree specimen about one year old and typical foliage specimens on a larger scale than they appear in the view of the tree specimen, all as depicted in color as nearly true as it is reasonably possible to make the same in an illustration of this type.

The following is a detailed description of my new variety of maple tree, with color terminology in accordance with the Exotica Horticultural Color Guide, published by Roehrs Company, of Rutherford, N.J.:

Parentage: Bud mutation or sport of the maple variety known as "Crimson King."
Propagation: Holds its distinguishing characteristics through succeeding propagations by budding.
Locality where grown and observed: Fairview, Oreg.
Tree: Medium size; upright; dense; hardy.
*Trunk.*—Stocky; smooth.
*Branches.*—Stocky; smooth; profuse; fastigiate-columnar. Color—Chocolate, Color No. 7. Lenticels—average for the species.
Foliage:
*Leaves.*—Thick. Quantity—profuse. Size—smaller than normal for the species. Length—average from about 8.0 cm. to 10.0 cm. at the age of 2 years. Width—average from about 10.0 cm. to 12.5 cm. at the age of 2 years. Shape—5-lobed, but having the appearance of being 3-lobed due to very small size of lower 2 lobes; somewhat truncate at base. Color—Upper surface—Maroon, Color No. 42+. Under surface—Near Bottle Green, Color No. 69. Margin—remotely dentate, with pointed teeth. Petiole—long. Glands—None.
Flower buds: None observed.
Flowers: None observed.

I claim:

1. A new and distinct variety of maple tree, substantially as herein shown and described, characterized particularly as to novelty by the unique combination of a more profuse branching habit than is normal for the species botanically known as *Acer platanoides* and commercially known as "Crimson King," with all branches being of an upright nature and making the tree a fastigiate or columnar type, smaller leaves than those typical of "Crimson King," and said leaves being more cupped in form, and although the leaves are 5-lobed, the lower 2 lobes are very small and make the leaves appear 3-lobed in effect.

No references cited.

ROBERT E. BAGWILL, Primary Examiner